United States Patent [19]

Epstein

[11] Patent Number: 4,493,564
[45] Date of Patent: Jan. 15, 1985

[54] CLINICAL INSTRUMENT FOR MEASURING PULSE RATE AND BODY TEMPERATURE

[76] Inventor: Saul Epstein, 14558 Deervale Pl., Sherman Oaks, Calif. 91403

[21] Appl. No.: 424,602

[22] Filed: Sep. 27, 1982

[51] Int. Cl.³ .................... H01L 35/00; A61B 5/02
[52] U.S. Cl. .................... 374/179; 128/736; 128/687
[58] Field of Search ............ 374/169, 106, 107, 116, 374/103, 104, 163, 179, 185; 128/687, 700, 706–708, 736, 681, 678, 679, 670, 671, 724, 688–690

[56] References Cited

U.S. PATENT DOCUMENTS

| 3,581,734 | 6/1971 | Croslin | 128/679 |
| 3,593,704 | 7/1971 | Schwab | 374/169 X |
| 3,851,320 | 11/1974 | Dahl | 128/689 X |
| 3,999,537 | 12/1976 | Noiles | 128/687 X |
| 4,036,211 | 7/1977 | Ueth et al. | 128/671 X |
| 4,248,244 | 2/1981 | Charnitski et al. | 128/706 |

Primary Examiner—Gerald Goldberg
Assistant Examiner—James R. Giebel

[57] ABSTRACT

A clinical instrument using a thermocouple probe for the measurement of pulse rate and body temperature using a single sensor. The variation in temperature due to heart beat found at the base of the tongue is detected with a fine wire thermocouple and timed. Pulse rate is calculated and displayed based on the time between beats. The DC component of the thermocouple output is digitized and displayed as body temperature.

9 Claims, 4 Drawing Figures

CLINICAL INSTRUMENT FOR MEASURING PULSE RATE AND BODY TEMPERATURE

BACKGROUND OF THE INVENTION

1. Field of the Invention.

This invention relates to instruments for determining human pulse rate and body temperature.

2. Prior Art.

Traditionally, pulse rate has been determined by feeling the pulsations of blood flowing at the wrist or other suitable spot on the body and counting their number for some predetermined time. This method is still almost universally used, although recently electronic pulse rate meters have made their appearance, primarily for use by joggers, etc. Such instruments, however, have not yet found acceptance in a hospital environment. The probable reasons for this are discussed below.

Electronic thermometers, on the other hand have found wide acceptance in hospitals. At this time, well over 50% of the temperature measurements made in hospitals are made by electronic thermometers. A clinical electronic thermometer typically uses a thermistor sensor and a disposable sheath to prevent cross infection. It takes some 30 to 45 seconds to make a body temperature measurement using electronic thermometers currently available.

It has been felt that since a nurse must be in attendance with a patient for 30 to 45 seconds anyhow, she might as well count the patient's pulse. An electronic pulse rate meter would be just one more item for the nurse to carry and would not save any time. Consequently, there has been no incentive for hospitals to invest in electronic pulse rate meters.

In a copending patent application Ser. No. 424,601, filed contemporaneously herewith, I have described an electronic thermometer suitable for clinical use with which it is practical to make temperature measurments in just a few seconds. If it is only necessary for the nurse to attend the patient for a few seconds, it will become desirable for hospitals to use electronic pulse rate meters, if same can be made convenient and economical.

It is thus an object of the present invention to provide a combined thermometer and pulse rate meter using a single transducer to sense both temperature and pulse rate.

It is a further object of the present invention to provide a novel means of measuring pulse rate.

SUMMARY OF THE INVENTION

As noted above, my copending application describes an electronic thermometer wherein rapid measurements of body temperature can be made. The sensor used is a fine wire bare bead thermocouple. The present invention utilizes such a thermometer for measuring temperature, and in addition detects the variation in the temperature of the sensor caused by blood flow pulsations, and derives pulse rate therefrom. I have found that the temperature of the tissue adjacent the base of the tongue to one side of the frenum increases slightly each time a pulse of blood flows. I have found that this increase is detectable by a fine wire thermocouple and can be used to monitor pulse rate. Thus, a simultaneous reading of body temperature and pulse rate can be obtained using but a single sensor.

DETAILED DESCRIPTION OF THE INVENTION

Figure 1:
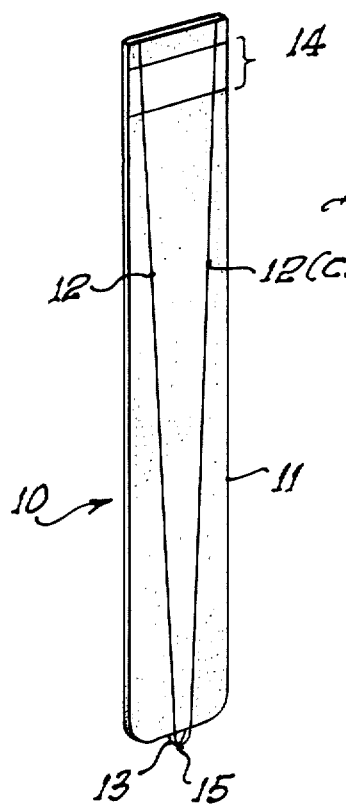
FIG. 1 is a perspective view of a thermocouple probe suitable for use with the present invention.
Figure 1A:
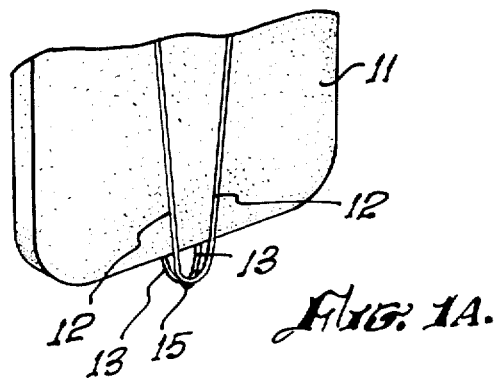
FIG. 1A is an enlarged view of the bottom portion of the probe of FIG. 1 presenting a clearer picture of the junction itself.

FIG. 1 depicts a bare bead thermocouple probe 10 such as would be suitable for use with the present invention. The probe includes a slat like body 11 preferably fabricated of plastic or cardboard, onto which thermocouple wire is adhered. A thermocouple junction is made at one end of the body and a connection area provided at the other. In the embodiment shown in FIG. 1, a length of Chromel 12 is looped along one surface of body 11 leaving a portion of the wire overhanging the end. A similar loop of Constantan 13 is looped along the obverse side of the body. Chromel and Constantan (a type E thermocouple) have been chosen for purposes of example, but it should be understood that other thermocouple materials could be used in practising the present invention if desired. The two lengths of thermocouple wire are adhered to the body as by taping or spraying with adhesive. A window 14 in the tape or adhesive is left near the connection end of the body to allow for electrical contact with the wires. At the junction end, the overhanging portions of the wires 12 and 13 are welded at the point furthermost from the body, forming the measuring junction 15. While the size of the thermocouple wire used is not critical, it can be appreciated that the finer the wire, the faster will be the response, but that too fine a wire will result in insufficient structural rigidity. Wire diameters of from 0.002 to 0.005 inches have been found to be most suitable but wire sizes outside this range may also be used.

Figure 2:
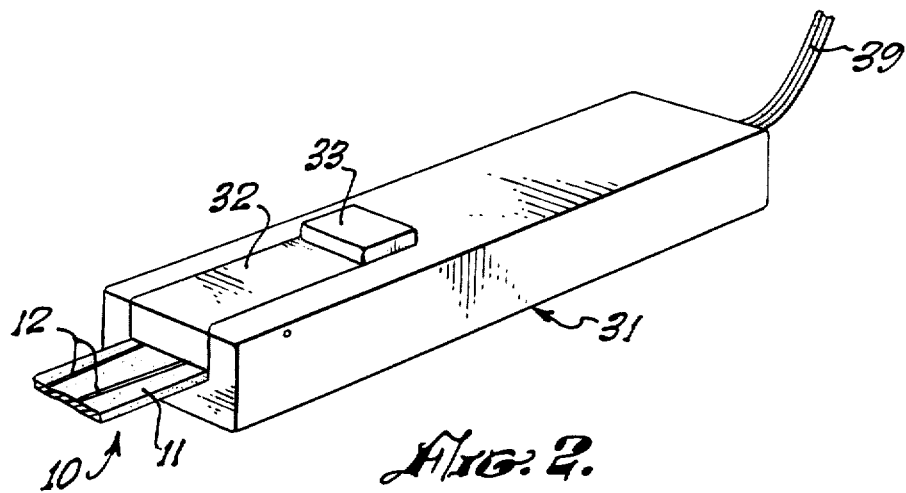
FIG. 2 is a perspective view of a probe holder for use with the probe of FIG. 1.
Figure 3:
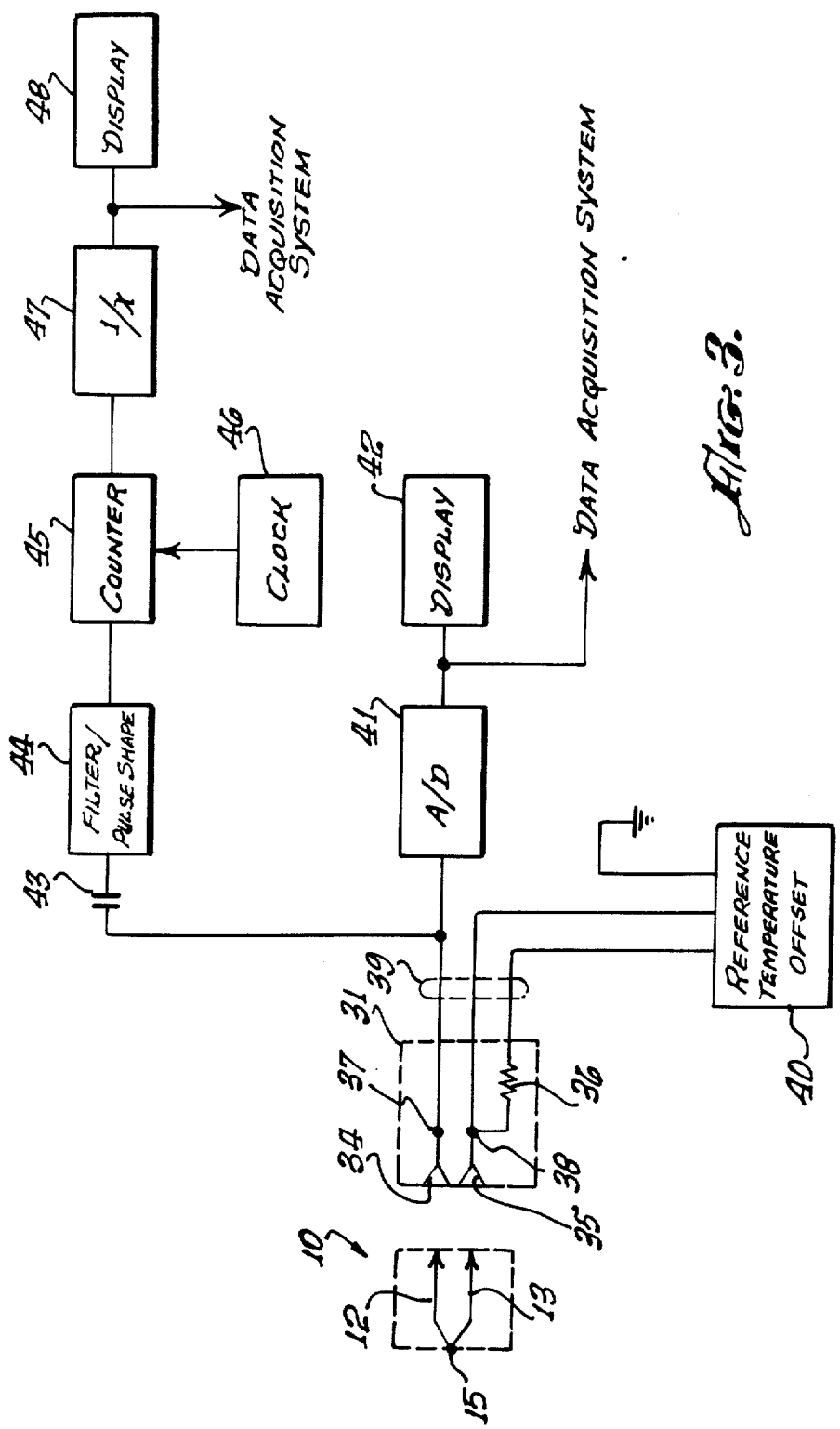
FIG. 3 is a block diagram of the circuitry of the present invention.

Probe holder 31, which is illustrated in FIG. 2, includes a pivoted clamp 32 which clamps the probe against the body of probe holder 31. Button 33 is depressed to open the clamp for insertion or removal of a probe. The probe holder contains contacts 34 and 35 for contacting the thermocouple wire at windows 14 on the probe 10. These contacts are preferably fabricated from thermocouple materials, but if the probe holder is carefully designed so that the thermal gradients between the contacts and resistor 36 (which is also contained within probe holder 31) are low, copper or another material might be used. If contacts 34 and 35 are made of thermocouple material, then the transition to copper is made at junctions 37 and 38. Thermocouple circuits are extremely low level circuits and care must be taken in design and fabrication to avoid temperature gradients and stray emfs. It is important that the temperature difference between resistor 36 and the points at which thermocouple material joins copper be very low, whether that be at contacts 34 and 35, or at junctions 37 and 38. Three conductor cable 39 connects the probe holder 31 to the signal conditioning circuitry.

The reference temperature offset circuit 40 in conjunction with temperature sensitive resistor 36, provides an offset voltage which sets the effective reference temperature (i.e., the measuring junction temperature which results in zero voltage to the measuring circuit) at the desired point and which varies with temperature so as to just counteract the varying voltage at junctions 37 and 38 as the temperature of the junctions varies.

Since the best thermometer accuracy is desired in the region of normal fever temperatures, it is preferable that the effective reference temperature be 98.6° F., but satisfactory temperature measurements can be made even if other effective reference temperatures are used.

One serious problem arises in using thermocouple probes for the measurement of clinical temperatures. That problem arises from the fact that even premium thermocouple wire does not have adequate uniformity to assure an accuracy of plus/minus 0.2° F. at normal fever temperatures. Consequently, either a manual or automatic adjustment of the offset voltage is required to compensate for variations in wire calibration. Details of how such an adjustment can be made is explained in my copending application referred to above.

The DC component of the sensor output is digitized in A/D converter 41 and the result either delivered to a data acquisition system or displayed in units of temperature by display 42.

Blocking capacitor 43 allows the AC component of the thermocouple signal to be coupled to the filter and pulse shaping circuit 44 where interfering signals are filtered out and the blood pulse shaped so that it can trigger counter 45. Counter 45 counts the number of clock pulses between successive blood pulses. CLK pulses are preferably at a frequency of 166.67 Hz since the reciprocal of the number of clock pulses between blood pulses is then decimally related to the pulse rate in beats per minute and this minimizes the computation required to obtain a display in beats per minute. Of course, the clock rate can be at any frequency desired so long as the required scaling is done at some point in the circuit. It is also not necessary that the counter count pulses between successive heart beats. Every other beat, every third beat, every fourth beat, or any other consistent number could be used. Such operation would result in averaging the pulse rate over 2, 3, 4, etc., heart beats. If averaging over more than one heart beat is desired, suitable dividers are inserted between pulse shaper 44 and counter 45 so that only the second, third or whatever submultiple of heart beats desired is transmitted to counter 45.

The number of clock pulses between beats is transmitted to block 47 where the reciprocal is calculated and transmitted in digital form to display 48 where the pulse rate is displayed in beats per minute. The output of reciprocal calculator 47 can, if desired, be transmitted to a data acquisition system.

To obtain readings of body temperature and pulse rate, the probe 10 is inserted into the back of the mouth under the tongue on one side or the other of the frenum. The junction 15 should be in contact with tissue at the base of the tongue. At this position, due to its rich blood supply and proximity to the carotid arteries, I have found that the temperature of the tissue increases slightly at each heart beat. The average temperature is, of course, what is known as body temperature. The probe output is divided into AC and DC components, the AC component being used for pulse rate determinations, and the DC component for temperature measurements as previously described.

What has been described is a clinical instrument suitable for making measurements of pulse rate and body temperature simultaneously using a single sensor. The principles disclosed can, of course, be used to provide a measure of pulse rate alone and such application is contemplated. This and other modifications of the present invention will readily occur to those skilled in the art and same are intended to be within the scope of the appended claims.

I claim:
1. A clinical instrument for measuring the pulse rate and body temperature of a patient which comprises:
   (a) a sensor for sensing the temperature of tissue said sensor having an electrical output with a DC component responsive to the average temperature of said tissue and an AC component responsive to pulses of blood;
   (b) means responsive to the DC component of the output of said sensor for providing an output representative of the temperature being sensed; and
   (c) means responsive to the AC component of the output of said sensor for providing an output representative of the pulse rate of said patient.

2. A clinical instrument as recited in claim 1 where said sensor is a thermocouple probe.

3. A clinical instrument as recited in claims 1 or 2 where said outputs are visual representations of temperature and pulse rate.

4. A clinical instrument for measuring the pulse rate of patient which comprises:
   (a) a temperature sensor for sensing the tissue temperature of said patient;
   (b) means responsive to said temperature sensor for providing electircal pulses coresponding to the heart beat of said patient;
   (c) a clock pulse generator;
   (d) means for counting the number of clock pulses between two or more of said electrical pulses; and
   (e) means responsive to the number of clock pulses between two or more of said electrical pulses for providing an output representative of the pulse rate of said patient.

5. A clinical instrument as recited in claim 4 where said temperature sensor is a thermocouple.

6. A clinical instrument as recited in claims 4 or 5 where said output is a visual representation of pulse rate.

7. A method of measuring pulse rate of a patient which comprises the steps of:
   (a) placing a temperature sensor at the base of the tongue of a patient to the side of the frenum whereby said sensor has an electrical output comprised of a DC and an AC component;
   (b) separating the AC component of the output of said sensor from the DC component; and
   (c) calculating the pulse rate of the patient as a function of the elapsed time between two or more maxima of sensor temperature.

8. A method of measuring pulse rate as recited in claim 7 where said sensor is a thermocouple.

9. A method of measuring pulse rate as recited in claims 7 or 8 and further including the step of displaying the calculated pulse rate on a digital display.

* * * * *